United States Patent [19]
Bryan et al.

[11] Patent Number: 4,980,288
[45] Date of Patent: Dec. 25, 1990

[54] SUBTILISIN WITH INCREASED THERMAL STABILITY

[75] Inventors: Philip N. Bryan, Silver Spring; Michele L. Rollence, Damascus; Michael W. Pantoliano, Silver Spring, all of Md.

[73] Assignee: Genex Corporation, Gaithersburg, Md.

[21] Appl. No.: 143,949

[22] Filed: Dec. 14, 1987

Related U.S. Application Data

[63] Continuation-in-part of Ser. No. 828,545, Feb. 12, 1986.

[51] Int. Cl.$^5$ .................. C12N 9/56; C12N 15/00; C12N 1/20; C07H 15/12
[52] U.S. Cl. .................. 435/222; 435/172.1; 435/172.3; 435/252.31; 435/320; 536/27; 252/174.12; 935/14; 935/29; 935/74
[58] Field of Search ............... 435/172.1, 172.3, 222, 435/252.31, 320; 536/27; 935/14, 29, 74; 252/174.12

[56] References Cited

U.S. PATENT DOCUMENTS

| | | | |
|---|---|---|---|
| 4,752,585 | 6/1988 | Koths et al. | 435/256 |
| 4,760,025 | 7/1988 | Estell et al. | 435/222 |
| 4,801,537 | 1/1989 | Nagarajan et al. | 435/68 |

OTHER PUBLICATIONS

International Search Report, PCT/US87/00348.
Estell, D. A. et al., *J. Biol. Chem.*, 260:6518–6521 (1985).
Liao, H. et al., *Proc. Natl. Acad. Sci USA* 83:576–580 (1986).
Estell, D. A. et al., *World Biotech Rep.* 2:181–187 (1984).
Vasantha, N. et al., *Genet. Biotechnol. Bacilli* 2:163–172 (1983).
Wells, J. A. et al., *Genet. Biotechnol. Bacilli* 2:173–180 (1983).
Shortle, D. et al., *Proc. Natl. Acad. Sci. USA* 75:2170–2174 (1978).
Vasantha, N. et al., *J. Bacteriol.* 159:811–819 (1984).
Jacobs, M. et al., *Nucl. Acids Res.* 13:8913–8926 (1985).
Nedkov, P. et al., *Biol. Chem. Hoppe-Seyler* 366:421–430 (1985).
Kurihara, M. et al., *J. Biol. Chem.* 247:5619–5631 (1972).
Svendsen, I. et al., *FEBS Letts.* 196:228–232 (1986).
Meloun, B. et al., *FEBS Lett.* 183:195–200 (1985).
Jany, K. D. et al., *Biol. Chem. Hoppe-Seyler* 366:485–492 (1985).
McPhalen, C. A. et al., *FEBS Lett.* 188:55–58 (1985).
Pahler, A. et al., *EMBO J.* 3:1311–1314 (1984).
Myers, R. M. et al., *Science* 229:242–247 (1985).
Folk, W. R. et al., *Cell* 33:585–593 (1983).
Pantoliano, M. W. et al., *Biochemistry* 26:2077–2082 (1987).
Bryan, P. N. et al., *Proteins: Structure, Function and Genetics* 1:326–334 (1986).
Cunningham, B. C. et al., *Protein Engineering* 1:319–325 (1987).
Bryan, P. et al., *Proc. Natl. Acad. Sci. USA* 83:3743–3745 (1986).
Wells, J. A. et al., *Nucl. Acids Res.* 11:7911–7925 (1983).

*Primary Examiner*—Thomas D. Mays
*Attorney, Agent, or Firm*—Saidman, Sterne, Kessler & Goldstein

[57] ABSTRACT

Cloned DNA is mutated by creating a single-stranded target region in a cloned DNA segment, and introducing a mutation into the single-stranded target region by treating the target region with a chemical or biological mutagenizing agent capable of introducing mutations into single-stranded DNA. The mutated target region then is rendered double-stranded and a microorganism is transformed with the mutated double-stranded DNA present in an expression vector. The transformed microorganism is cultivated under conditions wherein the mutated DNA is expressed to form an expression product, and the expression product is screened to identify a desired mutation in the DNA segment. Mutant subtilisins of enhanced thermal stability are also disclosed.

24 Claims, 8 Drawing Sheets

```
                   Ser
                   G
TAC GGG GCG TAC AAC GGT ACG TCA AGT
Tyr Gly Ala Tyr Asn Gly Thr Ser Met
    215                 220
```

SUBTILISIN WITH INCREASED THERMAL STABILITY

Cross Reference to Related Application

This is a continuation-in-part of application Ser. No. 828,545, filed in the U.S. on Feb. 12, 1986, the contents of which are fully incorporated herein by reference.

BACKGROUND OF THE INVENTION

1. Field of the Invention

The present invention relates to a method for mutating genetic material and screening mutant genetic material for a desired mutation. The invention further relates to mutant genetic material produced according to the disclosed method, as well as to expression products of such mutant genetic material.

2. Description of the Background Art

The largest class of naturally occurring proteins is made up of enzymes. Each enzyme generally catalyzes a different kind of chemical reaction, and is usually highly specific in its function. An enzyme molecule contains an active site to which a specific substrate is bound during a catalytic cycle.

Although there may be slight variations in a distinct type of naturally occurring enzyme within a given species of organism, enzyme molecules of a specific type produced by organisms of the same species generally are substantially identical with respect to substrate specificity, thermal stability, activity levels under various conditions (e.g., temperature and pH), oxidation stability, and the like. Such characteristics of a naturally occurring or "wild-type" enzyme are not necessarily optimized for utilization outside of the natural environment of the enzyme. It may thus be desirable to alter a natural characteristic of an enzyme to optimize a certain property of the enzyme for a specific use, or for use in a specific environment The amino acid sequence of an enzyme determines the characteristics of the enzyme, and the enzyme's amino acid sequence is specified by the nucleotide sequence of a gene coding for the enzyme. A change of the amino acid sequence of an enzyme may alter the enzyme's properties to varying degrees, or may even inactivate the enzyme, depending on the location, nature and/or magnitude of the change in the amino acid sequence.

Methods for introducing specific amino acid changes into proteins, such as oligonucleotide-directed mutagenesis of DNA, are known in the art. However, the ability to predict the effects of a specific mutation is poor, making the process of creating and characterizing desired mutations laborious.

Methods for random mutagenesis of genetic material are also known, but in the absence of a method for rapid and effective screening of a large number of mutants, identification of organisms having the desired mutation is tedious.

There remains a need in the art for new and practical mutagenesis and screening methods and for the products thereof.

Naturally occurring bacterial proteases are currently used for many purposes, among these is as an additive to washing preparations. Many stains on clothes are proteinaceous and wide-specificity proteases can substantially improve removal of such stains. Unfortunately, naturally-occurring proteases lose activity when stored in solution with detergents. Typically this decay of activity is geometric in nature, that is, a certain percentage of activity is lost in each time interval. The present invention provides a method to develop novel proteases with enhanced thermal stability and which survive prolonged storage in liquid detergents much longer than naturally-occurring proteases.

SUMMARY OF THE INVENTION

In accordance with the present invention, a method for mutating cloned DNA and thereafter identifying mutants comprises creating a single-stranded target region in a cloned DNA segment, and introducing a mutation into the target region by treating the target region with a chemical mutagenizing agent capable of introducing mutations into single-stranded DNA. The target region then is rendered double-stranded to form mutated double-stranded DNA, and a microorganism is transformed with an expression vector containing the mutated double-stranded DNA. The transformed microorganism is cultivated under conditions wherein the mutated DNA is expressed to form an expression product, and the expression product is screened to identify a desired mutation in the DNA segment.

DETAILED DESCRIPTION OF THE PREFERRED EMBODIMENTS

Figure 1:
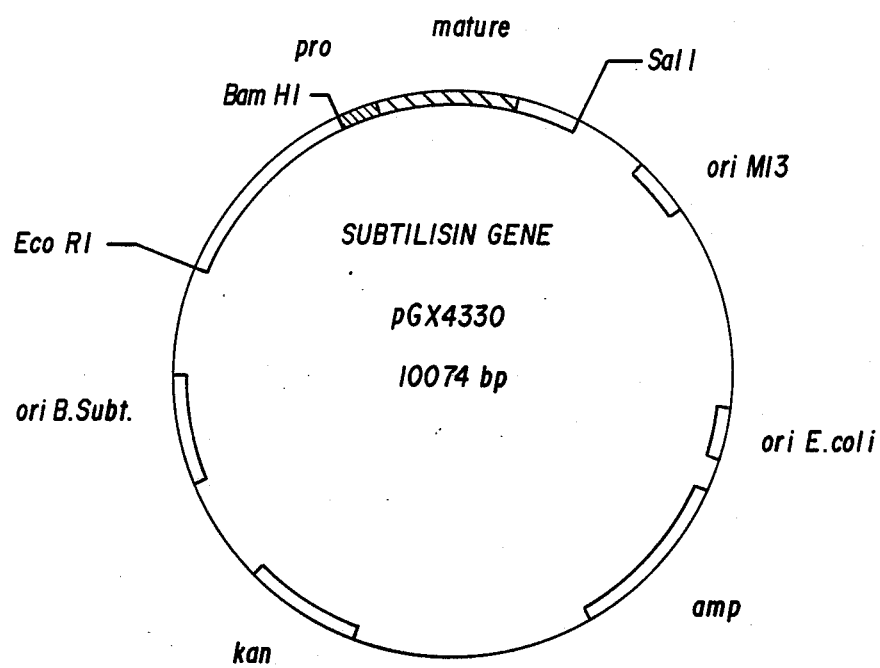
FIG. 1 is a schematic diagram showing the subtilisin gene cloned in plasmid pGX4330 for mutagenesis and screening according to the invention.

The present invention relates to modification of one or more characteristics of a protein, such as an enzyme, by mutating a nucleotide sequence (gene) coding for the protein and screening for desired mutations. Such modification can include enhancing or diminishing an enzyme's thermal stability, substrate specificity, oxidation stability, activity profile under varying conditions of pH and/or temperature, and the like.

Prior to mutation of a gene coding for an enzyme of interest, the gene generally is first isolated from its natural source and cloned in a cloning vector. Alternatively, mRNA which is transcribed from the gene of interest can be isolated from the source cell and converted into cDNA by reverse transcription for insertion into a cloning vector. A cloning vector can be a phage or plasmid, and generally includes a replicon for autonomous replication of the vector in a microorganism independent of the genome of the microorganism. A cloning vector advantageously includes one or more phenotypic markers, such as DNA coding for antibiotic resistance, to aid in selection of microorganisms transformed by the vector.

Procedures for insertion of DNA or cDNA into a vector for cloning purposes are well known in the art. These procedures generally include insertion of the gene of interest into an opened restriction endonuclease site in the vector, and may involve addition of homopolymeric tails of deoxynucleotides to the ends of the gene and linking the gene to opened ends of a cloning vector having complementary homopolymeric tails. A gene of interest present in a cloning vector can be mutated in accordance with the method of this invention.

In one embodiment, a gene of interest to be treated according to the invention is present in an expression vector. An expression vector generally falls under the definition of a cloning vector since an expression vector usually includes the components of a typical cloning vector, namely, one or more replicons as defined above, and one or more phenotypic markers for selection purposes. Additionally, an expression vector includes control sequences encoding a promoter, operator, ribosome binding site and translation initiation signal. For expression under the direction of the control sequences, a target gene to be treated according to the invention is operably linked with the control sequences in the proper reading frame.

An expression vector containing the DNA sequence to be targeted can be a phage or a plasmid, with plasmids being preferred.

According to one aspect of the invention, a method for mutating a cloned DNA segment and thereafter identifying mutants includes the step of providing a single-stranded target region in the cloned DNA segment. The target region can include the entire DNA segment of interest, or a portion thereof. The targeted portion can be randomly or specifically selected.

The target region of the DNA segment of interest is rendered single-stranded by any suitable method known in the art, such as the method disclosed in Shortle et al., Proc. Natl. Acad. Sci. USA, 75:2170-2174 (1978). Another method involves providing a single-stranded copy of a plasmid containing the DNA segment of interest, and annealing to the single-stranded copy a DNA fragment containing plasmid sequences but not including a segment complementary to the target region. This procedure creates a gapped duplex molecule with a single-stranded target region.

One or more mutations are introduced into the single-stranded target region by treating the target region with a chemical or biological mutagenizing agent (mutagen) capable of introducing mutations into single-stranded DNA. One such chemical mutagen is sodium bisulfite which causes G-C to A-T transitions only (wherein G, C, A or T refer respectively to guanine, cytosine, adenine and thymine). Other chemical or biological mutagens, such as hydroxylamine, nitrous acid, formic acid and hydrazine are suitable and can be used according to this invention.

Mutations are introduced at a controllable level, advantageously from one to about five changes per molecule, and a library of mutated plasmid-borne DNA is produced (e.g., by incubating DNA in 4M Na-bisulfite, pH 6.0 for 5 to 30 minutes). Advantageously, the library is large enough to generate up to $10^5$–$10^6$ different variants upon transformation into a microorganism, since a desired mutation may occur infrequently.

Alternatively, mutations are introduced into the cloned DNA by replication of the cloned DNA in a mutator strain of $E.$ $coli$, such as a Mut D strain of $E.$ $coli$ which produces a range of mutations due to its error prone DNA polymerase. In this method Mut D $E.$ $coli$ containing plasmid are grown at 37° C. in 250 ml culture in rich media containing 50 mg/ml thymine to an optical density at 650 nm of 0.6. The plasmid is amplified by the addition of 175 ug/ml chloramphenicol and continued incubation for 16 hours at 37° C.

After mutating the target region, the target region is rendered double-stranded by filling in the single-stranded region using DNA polymerase I (Klenow fragment) or reverse transcriptase, see, e.g., Shortle et al., supra.

A microorganism is transformed with the mutated double-stranded DNA present in an expression vector, the mutated DNA being operably linked to control sequences capable of directing expression of the mutated DNA in the transformed microorganism. The transformed microorganism then is cultivated under protein-producing conditions including necessary nutrients and physiologically acceptable pH and temperature, such that the mutated DNA is expressed to form an expression product.

The method according to this invention can be used to mutate serine proteases to enhance certain characteristics, particularly thermal stability. A protease is a catalyst for the cleavage of peptide bonds.

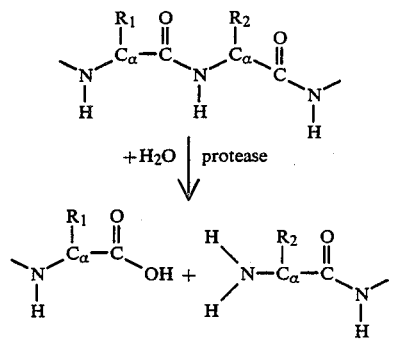

A serine protease is an enzyme which calatyzes the hydrolysis of peptide bonds in which there is an essential serine residue at the active site. Serine proteases can be inhibited by phenylmethanesulfonylfluoride and by diisopropylfluorophosphate. A subtilisin is a serine protease produced by Gram positive bacteria or fungi. The amino acid sequences of seven subtilisins are known. These include five subtilisins from Bacillus strains (subtilisin BPN', subtilisin Carlsberg, subtilisin DY, subtilisin amylosacchariticus, and mesenticopeptidase).

(Vasantha et al., "Gene for alkaline protease and neutral protease from *Bacillus amyloliquefaciens* contain a large open-reading frame between the regions coding for signal sequence and mature protein," *J. Bacteriol.* 159:811–819 (1984); Jacobs et al., "Cloning sequencing and expression of subtilisin Carlsberg from *Bacillus licheniformis*," *Nucleic Acids Res.* 13:8913–8926 (1985); Nedkov et al., "Determination of the complete amino acid sequence of subtilisin DY and its comparison with the primary structures of the subtilisin BPN', Carlsberg and amylosacchariticus," *Biol. Chem. Hoppe-Seyler* 366:421–430 (1985); Kurihara et al., "Subtilisin amylosacchariticus," *J. Biol. Chem.* 247:5619–5631 (1972); and Svendsen et al., "Complete amino acid sequence of alkaline mesentericopeptidase," *FEBS Lett.* 196:228–232 (1986)).

The amino acid sequence of the subtilisin thermitase from *Thermoactinomyces vulgaris* is also known. (Meloun et al., "Complete primary structure of thermitase from thermoactinomyces vulgaris and its structural features related to the subtilisin-type proteanases," *FEBS Lett.* 183:195–200 (1985).)

The amino acid sequences from two fungal proteases are known: proteinase K from *Tritirachium album* (Jany et al., "Proteinase K from Tritirachium albam Limber," *Biol. Chem. Hoppe-Sevler* 366:485–492 (1985)) and thermomycolase from the thermophilic fungus, *Malbranchea pulchella* (Gaucher et al., "Endopeptidases: Thermomycolin," *Methods Enzymol.* 45:415–433 (1976)).

These enzymes have been shown to be related to subtilisin BPN', not only through their primary sequences and enzymological properties, but also by comparison of x-ray crystallographic data. (McPhalen et al., "Crystal and molecular structure of the inhibitor eglin from leeches in complex with subtilisin Carlsberg," *FEBS Lett.* 188:55–58 (1985) and Pahler et al., "Three-dimensional structure of fungal proteinase K reveals similarity to bacterial subtilisin," *EMBO J.* 3:1311–1314 (1984).)

As used in this invention, the term "subtilisin material" is a proteinaceous material which contains a subtilisin as its active ingredient. As used herein, and under the definition of subtilisin material, any serine protease is a subtilisin which has at least 30%, preferaby 50%, and more preferably 80% amino acid sequence homology with the sequences referenced above for subtilisin BPN', subtilisin Carlsberg, subtilisin DY, subtilisin amylosacchariticus, mesenticopeptidase, thermitase, proteinase K, and thermomycolase. These serine proteases are also described herein as "homologous serine proteases.+

According to one embodiment, *B. subtilis* is transformed by an expression vector carrying the mutated DNA. If expression is to take place in a secreting microorganism such as *B. subtilis*, a single sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when it is present.

For screening mutants, transformed *B. subtilis* is cultivated in the presence of a filter material (such as nitrocellulose) to which the secreted expression product (e.g., enzyme) binds. In order to screen for an expression product having a desired characteristic, filter bound expression product is subjected to conditions which distinguish expression product of interest from wild-type expression product. For example, the filter-bound expression product can be subjected to conditions which would inactivate a wild-type expression product. The treated expression product can thereafter be contacted with a substrate of the enzyme, and enzyme activity with the substrate identifies an expression product with enhanced stability and thereby a desired mutation.

Although the invention will further be specifically described with respect to production of thermally stable variants of the Bacillus serine protease, subtilisin BPN', it is to be understood that the present invention is equally applicable to modification of the characteristics of other proteins. In particular, other homologous serine proteases from other microorganisms may be mutated and screened according to this invention. These homologous serine proteases may include, but are not limited to, those from other Bacillus strains such as subtilisin Carlsberg from *Bacillus licheniformis*, subtilisin DY, subtilisin amylosacchariticus, and mesentericopeptidase. Fungal proteases, such as protease K and thermomycolase may also be used, as well as mammalian proteases produced in a bacterial host.

For mutating subtilisin genetic coding sequences and isolating variant subtilisin proteins of enhanced thermal stability, the subtilisin gene from a Bacillus species including the natural promoter and other control sequences is cloned into a plasmid vector containing replicons for both *E. coli* and *B. subtilis*, a selectable phenotypic marker, and the M13 origin of replication for production of single-stranded plasmid DNA upon superinfection with helper phage IR1. Single-stranded plasmid DNA containing the cloned subtilisin gene is isolated and annealed with a DNA fragment containing vector sequences but not the coding region of subtilisin, to create a gapped duplex molecule. Mutations are introduced into the subtilisin gene either with sodium bisulfite, nitrous acid, or formic acid or by replication in a mutator strain of *E. coli* as described above. Since sodium bisulfite reacts exclusively with cytosine in single-stranded DNA, the mutations created with this mutagen are restricted only to the coding regions. Reaction time and bisulfite concentration are varied in different experiments such that from one to five mutations are created per subtilisin gene on average. Incubation of 10 ug of gapped duplex DNA in 4M Na-bisulfite, pH 6.0, for 8 minutes at 37° C. in a reaction volume of 400 ul, deaminates about 1% of cytosines in the single-stranded region. The coding region of mature subtilisin contains about 200 cytosines, depending on the DNA strand. Advantageously, the reaction time is varied from about 4 minutes (to produce a mutation frequency of about one in 200) to about 20 minutes (about 5 in 200).

After mutagenesis, the gapped molecules are treated in vitro with DNA polymerase I (Klenow fragment) to make fully double-stranded molecules and to fix the mutations. Competent *E. coli* are then transformed with the mutagenized DNA to produce an amplified library of mutant subtilisins. Amplified mutant libraries can also be made by growing the plasmid DNA in a Mut D strain of *E. coli* which increases the range of mutations due to its error prone DNA polymerase.

The mutagens, nitrous acid and formic acid may also be used to produce mutant libraries. Because these chemicals are not as specific for single-stranded DNA as sodium bisulfite, the mutagenesis reactions are performed according to the following procedure. The coding portion of the subtilisin gene is cloned into M13 phage by standard methods and single-stranded phage DNA prepared. The single-stranded DNA is then reacted with 1M nitrous acid pH 4.3 for 15–60 minutes at 23° C. or 2.4M formic acid for 1–5 minutes at 23° C. These ranges of reaction times produce a mutation frequency of from 1 in 1000 to 5 in 1000. After mutagenesis, a universal primer is annealed to the M13 DNA and duplex DNA is synthesized using the mutagenized single-stranded DNA as a template so that the coding portion of the subtilisin gene becomes fully double-stranded. As this point the coding region can be cut out of the M13 Vector with restriction enzymes and ligated into an unmutagenized expression vector so that mutations occur only in the restriction fragment. (Myers et al., Science 229:242–247 (1985)).

To screen for thermostability, a library of subtilisin variants should be produced which is large enough to generate approximately $5 \times 10^4$ random subtilisin variants or more upon transformation into B. subtilis, since mutations resulting in enhanced thermal stability occur infrequently.

After mutagenesis, the variant library is used to transform B. subtilis which will both express and secrete subtilisin. The subtilisin-bearing plasmid advantageously contains a high copy B. subtilis replicon and is capable of producing subtilisin at a high level in a Bacillus host. To screen for stable variants, a protease deficient B. subtilis strain is transformed with the variant plasmid library and plated out as follows: A nitrocellulose filter is placed on a nutrient base in a petri dish, and a cellulose acetate filter is placed on top of the nitrocellulose. Colonies are grown on the cellulose acetate, and subtilisin from individual colonies is secreted through the cellulose acetate onto the nitrocellulose filter where it is stably bound. Subtilisin from hundreds of colonies is bound to a single filter allowing subsequent screening of thousands of different variants by processing multiple filters.

To identify colonies producing subtilisin of enhanced thermal stability, the filters are incubated at 70° C. for 30 minutes in buffer solution to inactivate substantially all wild-type subtilisin activity. Variant subtilisins of enhanced stability retain activity after this heating step. When stable variants have been further mutagenized to screen for additional increases in stability, higher temperatures of longer incubation times must be used to inactivate the background activity. The heat-treated filter then is soaked in a solution containing Tosyl-L-Arg methyl ester (TAME) (Sigma) and the pH indicator phenol red (Kodak). Because TAME is a substrate for subtilisin it is cleaved in zones on the filter containing variant subtilisins which remain active after thermal treatment. As cleavage occurs, protons are released in the reaction and cause phenol red to change in color from red to yellow in areas retaining protease activity.

This procedure can be used to screen for other classes of variants with only slight modifications. For example, the filters could be treated at high pH, with denaturants, oxidizing agents, or under other conditions which normally inactivate an enzyme such as subtilisin, to find resistant variants. Variants with altered substrate specificity could be screened by replacing TAME with other substrates which are normally not cleaved by wild-type subtilisin.

Once a variant of enhanced stability is identified by screening, the colony from which the variant is derived is isolated and the altered subtilisin is purified. Experiments can be performed on the purified enzyme to determine conditions of thermal inactivation, denaturation temperature, kinetic parameters as well as other physical measurements. The altered gene can also be sequenced to determine the amino acid changes responsible for the enhanced stability. Using this procedure, variants showing a one-and-one-half to eight-fold improvement in resistance to thermal inactivation at 65° C. have been isolated. Thermally stable subtilisin is useful in laundry cleaning compositions.

It has surprisingly been found that substituting another amino acid for asparagine at amino acid position 218 of subtilisin enhances the thermal stability of subtilisin. Without being bound to. any particular theory, it is believed that substitution of serine for asparagine at position 218 stabilizes subtilisin by increasing the change in free energy for the unfolding reaction. According to one embodiment of this invention, the present invention relates to a cloned mutant subtilisin gene coding for a subtilisin material with serine substituted for asparagine at amino acid position 218 of subtilisin. This variant, produced by strain GX7150, has been designated 7150. This invention also includes other amino acid substitutions at the amino acid position 218 of subtilisin, especially aspartic acid.

In another embodiment of this invention, the gene coding for a subtilisin material contains serine or aspartic acid at amino acid position 218 and the subtilisin gene may also contain one or more additional amino acid substitions. Among the preferred additional amino acid substitutions in the cloned mutant 218-substituted subtilisin gene are the following random mutated subtilisin variants produced by the indicated strains:

| STRAIN | AMINO ACID SUBSTITUTION(S) | VARIANT |
|---|---|---|
| GX7169 | ASN218 → SER<br>GLY131 → ASP | 7169 |
| GX8301 | ASN218 → SER<br>THR254 → ALA | 8301 |
| GX8306 | ASN218 → SER<br>GLY166 → SER | 8306 |
| GX8315 | ASN218 → SER<br>GLY131 → ASP<br>THR254 → ALA | 8315 |

Other substitutions which increase the thermal stability of substilisin are:

| STRAIN | SUBSTITUTION(S) | VARIANT |
|---|---|---|
| GX7142 | ALA116 → THR<br>GLY131 → ASP | 7142 |
| GX7148 | GLY131 → ASP | 7148 |
| GX7178 | SER188 → PRO | 7178 |
| GX7188 | ALA116 → GLU | 7188 |
| GX7189 | LEU126 → ILE | 7189 |
| GX8305 | SER53 → THR | 8305 |

All of the amino acid substitutions given above were produced by random mutagenesis and screened according to this invention. Once the random mutations are made and identified, the mutation can be repeated and reproduced by oligonucleotide-directed mutagenesis. Furthermore, when more than one stabilizing mutation is introduced into the subtilisin molecule, the effects of those changes appear to be additive in free energy.

In addition to the subtilisin gene, genes for other serine proteases or other types of enzymes may be mutagenized to produce products with enhanced characteristics.

In addition to applying the method as described to other serine proteases, one can use the information obtained from one serine protease, subtilisin BPN' for example, to improve other proteases which are closely related, subtilisin Carlsberg for example. Closeness of relation is measured by comparison of amino-acid sequences. There are many methods of aligning protein sequences, but the differences are only manifest when the degree of relatedness is quite small. The methods described in *Atlas of Protein Sequence and Structure,* Margaret 0. Dayhoff editor, Vol. 5 Supplement 2, 1976, National Biomedical Research Foundation, Georgetown University Medical Center, Washington, D.C., p. 3 ff., entitled SEARCH and ALIGN, define relatedness. As is well known in the art, related proteins can differ in number of amino acids as well as identity of each amino acid along the chain. That is, there can be deletions or insertions when two structures are aligned for maximum identity. For example, subtilisin Carlsberg has only 274 amino acids, while subtilisin BPN' has 275 amino acids. Aligning the two sequences shows that Carlsberg has no residue corresponding to ASN56 of subtilisin BPN'. Thus the amino acid sequence of Carlsberg would appear very different from BPN' unless a gap is recorded at location 56. Therefore, one can predict with high degree of confidence that substituting SER for ASN at location 218 of subtilisin Carlsberg will increase thermal stability, provided that the residues in Carlsberg are numbered by homology to BPN'.

When one of the two homologous subtilisins has a gap, one must infer that the structures are different at that locality. Examples of such differences are well known in the art. Because of these local differences, one should not transfer stabilizing mutations if either subtilisin has a gap at, or immediately adjacent, to the site of the mutation. Therefore, after aligning the amino acid sequences, those mutations at or next to gaps are deleted from the list of desirable mutations and the mutation is not made.

One can use this reasoning to transfer all of the randomly-obtained stabilizing mutations described herein to other homologous serine proteases.

The stabilizing mutations found by the random mutagenesis method reveal that the structure of the enzyme being studied is not optimal at that location. The random method usually changes very few bases within the gene. Usually only one base is changed within a given codon; thus, one cannot go from any one amino acid to all other amino acids. For example, the codons for ASP (GAT and GAC) can be changed by single-base changes to (CAT, TAT, AAT, CAC, TAC, AAC, GGT, GTT, GCT, GGC, GTC, GCC, GAA, or GAG) which code for HIS, TYR, ASN, GLY, ALA, VAL, or GLU, but not to PHE, LEU, ILE, MET, THR, SER, CYS, LYS, ARG, GLN, TRP, or PRO.

Once the random method has shown that a given site is not optimal, oligonucleotide-directed mutagenesis can be used to introduce each of the remaining 18 amino acids at that site. These mutants can then be tested for improved properties.

The mutant subtilisin material of this invention can be used as an additive to washing preparations, such as detergents, which are used for cleaning, in particular for cleaning clothes. The mutant subtilisin material of this invention is more thermally stable than wild-type subtilisin material and thus does not lose activity as rapidly as wild-type when stored in solution with detergents or when subjected to high heat during use in cleaning. By use of the mutant subtilisin material of this invention as an additive in washing preparations, the removal of proteinaceous stains on fabric is improved. The amount of mutant subtilisin material that may be used as an additive to washing preparations are well known in the art, or may readily be ascertained by routine experimentation. The optimal range of enzyme concentration will, of course, be related to the cost of the enzyme and the amount of cleaning needed.

The invention is illustrated by the following examples which are not intended to be limiting.

EXAMPLE I

Mutagenesis of Subtilisin

Figure 2:
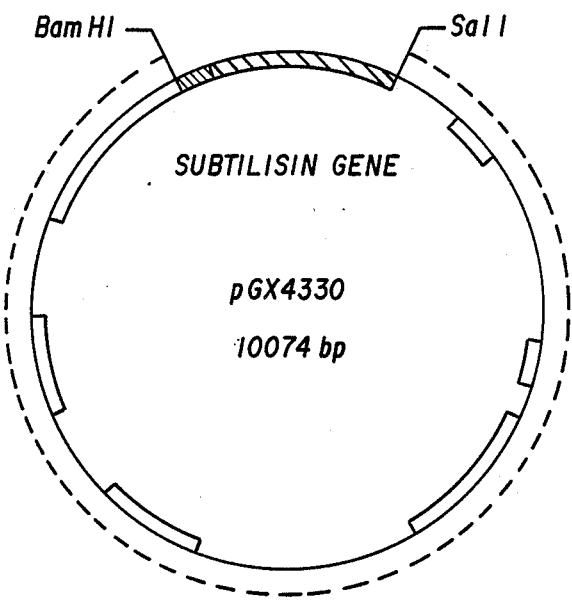
FIG. 2 is a schematic diagram showing a gapped duplex DNA molecule for mutagenesis according to the invention.

For mutagenesis, the subtilisin gene from *Bacillus amyloliquefaciens* including the natural promoter sequences was isolated (Vasantha et al. (1984) *J. Bacteriology* 159:811–819) and cloned into a vector (pGX4330, FIG. 1) containing the betalactamase gene and replicon from pBR322 for growth in *E. coli;* the kanamycin nucleotidyl transferase gene and replicon from pUB110 for growth in *B. subtilis;* and the M13 origin of replication for production of single-stranded plasmid DNA upon superinfection with helper phage IR1. Mutations were introduced into the subtilisin gene either with sodium bisulfite or by replication in a mutator strain of *E. coli.* Sodium bisulfite mutations were restricted to the subtilisin coding region using a variation of the method of Folk and Hofstetter (1985) *Cell* 33:585–593). Single-stranded plasmid DNA was annealed with a DNA fragment containing vector sequences but not the coding region of subtilisin to create a gapped duplex molecule (FIG. 2). One ug of single-stranded pGX4330 was mixed with 1 ug of double-stranded pGX4330 cut with BamHI and SalI in 50 mM NaCl, 50 mM Tris-HCl pH 8.0, 10 mM $MgCl_2$ in a volume of 15 ul. The DNA was heated to 90° C. in a boiling water bath for 5 minutes and allowed to anneal at 60° C. for 10 minutes. The gapped duplex was reacted with sodium bisulfite pH 6.0 in a volume of 400 ul at 37° C. Reaction time was varied from four to twenty minutes to produce an average of one to five mutations per gene. Since sodium bisulfite reacts exclusively with cytosine in single-stranded DNA, the mutations were restricted only to the subtilisin coding region. After mutagenesis, the gapped molecules were treated in vitro with DNA polymerase I (Klenow fragment) using well known techniques (see, e.g., Folk and Hofstetter, to make fully double-stranded molecules and to fix the mutations. Competent *E.* coli then were transformed with the mutagenized DNA using standard procedures (see, e.g., Maniatis et al. (1983) "Molecular Cloning: A Laboratory Manual," Cold Spring Harbor Press) to produce an amplified library of mutant subtilisins. Libraries were also made by growing pGX4330 in a Mut D strain of *E. coli* which produces a wider range of mutations due to its error prone DNA polymerase.

EXAMPLE II

Expression and Secretion in B. subtilis and Screening for Altered Stability

The variant library produced in Example I was used to transform *B. subtilis* strain GX4935, which will both express and secrete subtilisin. The subtilisin bearing plasmid contains a high copy *B. subtilis* replicon and is capable of producing subtilisin at a high level in a Bacillus host. To screen for stable variants, apr⁻, npr⁻, *B.*

*subtilis* strain GX4935 was transformed with the variant plasmid library and plated out as follows. Two filters were placed on Tryptose Blood Agar Base plus 10 ug/ml kanamycin plates. A nitrocellulose filter was laid directly on the agar and a cellulose acetate filter was placed on top of it. Colonies grown on the top filter secreted subtilisin through the permeable cellulose acetate onto the nitrocellulose where it was stably bound. Subtilisin from hundreds of colonies was bound to a single filter allowing subsequent screening of thousands of different variants by processing multiple filters.

Filters with subtilisin bound thereto were incubated at 70° C. in 10 mM $CaCl_2$, 10 mM Tris-HCl pH 8.0 for 30 minutes which inactivates substantially all native or wild-type subtilisin activity. Variant proteases of enhanced stability retain activity after the heating step.

To detect filter-bound protease activity, the filters were soaked in a solution containing Tosyl-L-Arg methyl ester (TAME) (10mM) and the pH indicator phenol red (1 mM) titrated to pH 9.0. TAME is a good substrate for subtilisin and is cleaved in zones on the filter containing active subtilisin. During the procedure, as cleavage occurred, protons were released in the reaction, causing phenol red to change in color from red to yellow in areas of protease activity. This assay procedure distinguishes thermally stable variants.

EXAMPLE III

Primary Characterization of Stable Variants

Figure 3:
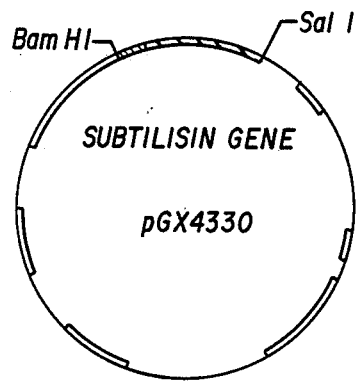
FIG. 3 is a portion of the variant subtilisin DNA sequence showing the single base substitution in the subtilisin gene which produces subtilisin of enhanced thermal stability according to the invention.

Once candidates were identified by filter screening, the corresponding colonies from the cellulose acetate filter were grown in liquid culture (2% yeast extract, 10 ug/ml kanamycin) for 18 hours. Under these conditions, subtilisin was secreted into the culture broth at 0.5–1.0 mg/ml and represents >80% of the total extracellular protein detectable by SDS polyacrylamide gel electrophoresis. The variant subtilisins were tested for resistance to thermal inactivation in solution. Culture supernatant was diluted 20-fold into either 10 mM $CaCl_2$, 50 mM Tris-HCl pH 8.0 or 5mM EDTA 50 mM Tris-HCl pH 8.0. In the presence of calcium, which greatly stabilizes subtilisin, samples were incubated at 65° C. and at time intervals up to 90 minutes, aliquots were removed and activity was measured at 37° C. using Azocoll as a substrate. In the presence of EDTA timepoints were taken after incubation at 45° C. Variants whose half-time of thermal inactivations was greater than 150% of wild-type subtilisin were of interest and further characterized. To confirm that stable subtilisin phenotypes resulted from plasmid-borne mutations, plasmid from positive colonies was purified and used to retransform *B. subtilis*. In almost all cases, the retransformed *B. subtilis* behave as the original isolate. To sequence the stable variant genes, the plasmid was used to transform *E. coli* and single-stranded template was made by superinfecting with phage IR1 according to the procedures described in (Dente et al. (1983) *Nucleic Acids Res.*, 11:1645–1655). One variant (GX7150, deposited with American Type Culture Collection, Rockville, Maryland as ATCC No. 53459) that produces a thermally stable subtilisin was shown to have a single base change in the cloned subtilisin gene resulting in a substitution of asparagine 218 with serine (see FIG. 3). To ensure that the enhanced stability resulted solely from this change, the mutation was introduced into wild-type subtilisin by oligonucleotide-directed mutagenesis using standard procedures (see, e.g., Zoller and Smith (1983), *Methods in Enzymology*, 100:468–500). The resulting subtilisin variant was shown to behave exactly like random isolate variant subtilisin produced by GX7150.

EXAMPLE IV

Physical and Chemical Properties of Subtilisin Produced by B. Substilis Strain GX7150

Purification

Subtilisin produced by GX7150 as described above, where asparagine 218 has been changed to serine was purified from cell-free fermentation broths by means of the following three-step purification scheme:

(1) DEAE chromatography of crude fermentation broth. The broth was adjusted to pH 7.0 by addition of solid 2-(N-morpholino)ethanesulfonic acid (Mes) and loaded onto a bed (13×5 cm) of DE-52 cellulose (Whatman) which was previously equilibrated with 20 mM Mes buffer (pH 7.0). Subtilisin washes through unretarded under these conditions.

(2) Acetone fractionation of DEAE eluate. Acetone (−20° C.) was stirred with the DEAE eluate at 4° C. The subtilisin precipitates between 50 and 70% acetone. The fraction the precipitates between 0 and 50% acetone was discarded.

(3) SE-53 (Whatman) chromatography of acetone precipitate. The acetone precipitated subtilisin was dissolved in 20 mM Mes buffer (pH 6.0) and loaded onto a column (2.5×16 cm) of SE-53 cellulose equilibrated with the same buffer. A linear salt gradient (0 to 0.2 M NaCl) was used to elute the subtilisin.

Fractions containing the highest specific activities were pooled and stored at −20° C. either as 70% isopropanol or 50% ammonium sulfate precipitants.

Enzyme Assay

Subtilisin activity was assayed by monitoring the hydrolysis of 1 0 mM solutions of the substrate, succinyl(L)-Ala-(L)-Ala-(L)-Pro-(L)-Phe-p-nitroanilide (SAAPF-pNA (Calbiochem)), in 50 mM Tris-HCl (pH 8 0), 50 mM KCl at 25.0° C. One unit of activity corresponds to the amount to enzyme that hydrolyzes 1 umole of substrate per min. under these conditions. One of the products of hydrolysis, p-nitroanilide, has an extinction coefficient of 8800 $M^{-1}cm^{-1}$ at 410 nm, thus allowing easy monitoring of the enzymatic reaction (Delmar et al. (1979) *Anal. Biochem.*, 99:316–320). Subtilisin concentrations were estimated at 280 nm using $E_0(0.1\%)=1.17$ (Ottesen & Svendson (1976) *Methods in Enzymology*, p. 207).

Kinetics of Thermal Inactivation

Thermal inactivation studies were performed by incubating a subtilisin solution (0.05 mg/ml) dissolved in a buffer of choice (usually 50 mM Tris-HCl (pH 8 0), 50 mM KCl) at some particular temperature. The sample was placed in a glass Durham tube which was immersed in a thermostated circulated water bath equilibrated at the temperature of choice. Evaporation from the sample tube was prevented by sealing with Parafilm Aliquots (10 ul) were removed at various time points and assayed by dilution into 1.0 ml of assay rolution at 25° C. The time zero measurement was the rate of hydrolysis of SAAPF-pNA before the sample is immersed in the temperature bath. All subsequent rates of hydrolysis of substrate were measured after immersion in the bath.

Differential Scanning Calorimetry

Differential scanning calorimetry data was obtained with a Hart Scientific instrument interfaced with an IBM personal computer (model XT) and controlled with DSC Software (Hart Scientific) and the Xenix operating system (Microsoft-Santa Cruz Operations). The temperature was increased from the starting point of 20° C. to 90° C. at a rate of 60° C./hr The protein concentration was 3.0 mg/ml.

Isoelectric Focusing

Analytical electrofocusing of subtilisin in thin layers of polyacrylamide was performed using known techniques, see, e.g. Winter et al. (1977) LKB Application Note 250. Ready-made acrylamide gels, Ampholine PAG plates (pH 3.0–9.5) were purchased from LKB, and the calibration standards (pH 5.0–10.5) were purchased from Pharmacia. The subtilisin samples were inactivated with phenylmethylsulfonylfluoride (PMSF) before loading onto the gels in order to prevent autolysis during electrofocusing.

Results

The purified subtilisin 7150 was found to have an isoelectric point of 8.8, essentially indistinguishable from that of the wild-type enzyme. Only a minor contaminant with an isoelectric point of 8.3 was detected. This level of homogeneity is comparable to that of the wild type.

The specific activity of subtilisin 7150 towards a peptide substrate was observed to be 120±5 Units/mg. This is 50% higher than that observed for the wild type: 80±5 Units/mg, an average for more than two dozen separate isolates. This difference is due to small changes in the kinetic parameters for hydrolysis of the substrate rather than a more highly purified preparation

Thermal Inactivation

Figure 4:
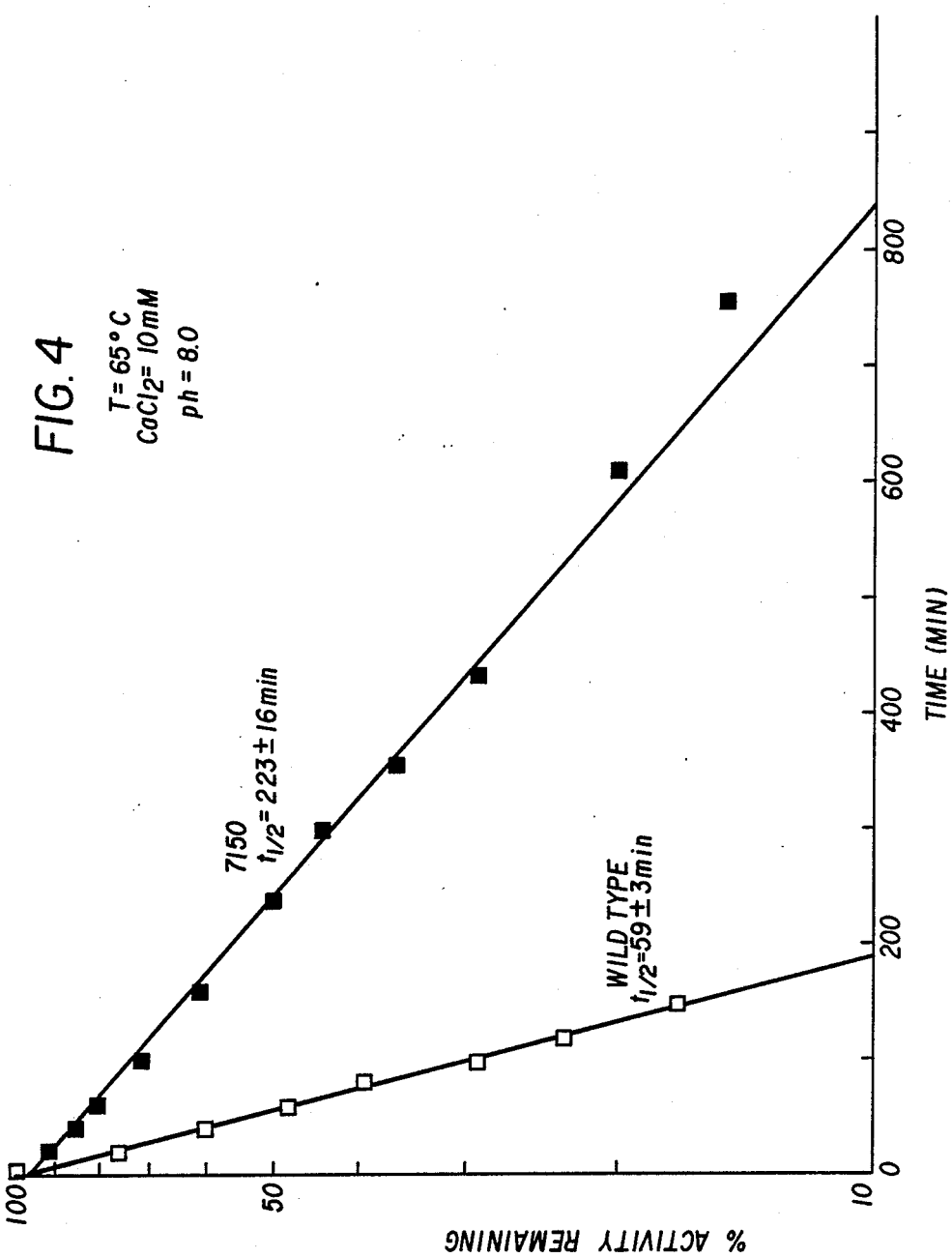
FIG. 4 is a graphic illustration showing thermal inactivation of variant subtilisin according to the invention (7150) and subtilisin wild-type at 65° C. in 10 mM $CaCl_2$, 50 mM KCl, 50 mM Tris-HCl, pH 8.0.

Plots of the logarithm of the remaining activity versus time were found, for the most part, to be linear over the course of three half-lives Thus, a first order rate law is applicable. This is illustrated in FIG. 4 which shows the rate of loss of activity for subtilisin 7150 and the wild-type enzyme at 65° C. in the presence of 10 mM $CaCl_2$, 50 mM KCl, and 50 mM Tris-HCl, pH 8.0. Under these conditions, the wild-type enzyme was found to have a half-life of 59±3 minutes which agrees well with that reported in the literature for similar conditions (Voordouw et al. (1976) Biochemistry, 3716–3724). The results for subtilisin 7150 reveal that this enzyme has a half-life of 223±16 minutes, almost four times that of the wild type. This is a clear demonstration that the single amino acid change of asparagine 218 to serine dramatically increases the kinetic thermal stability of subtilisin.

Figure 5:
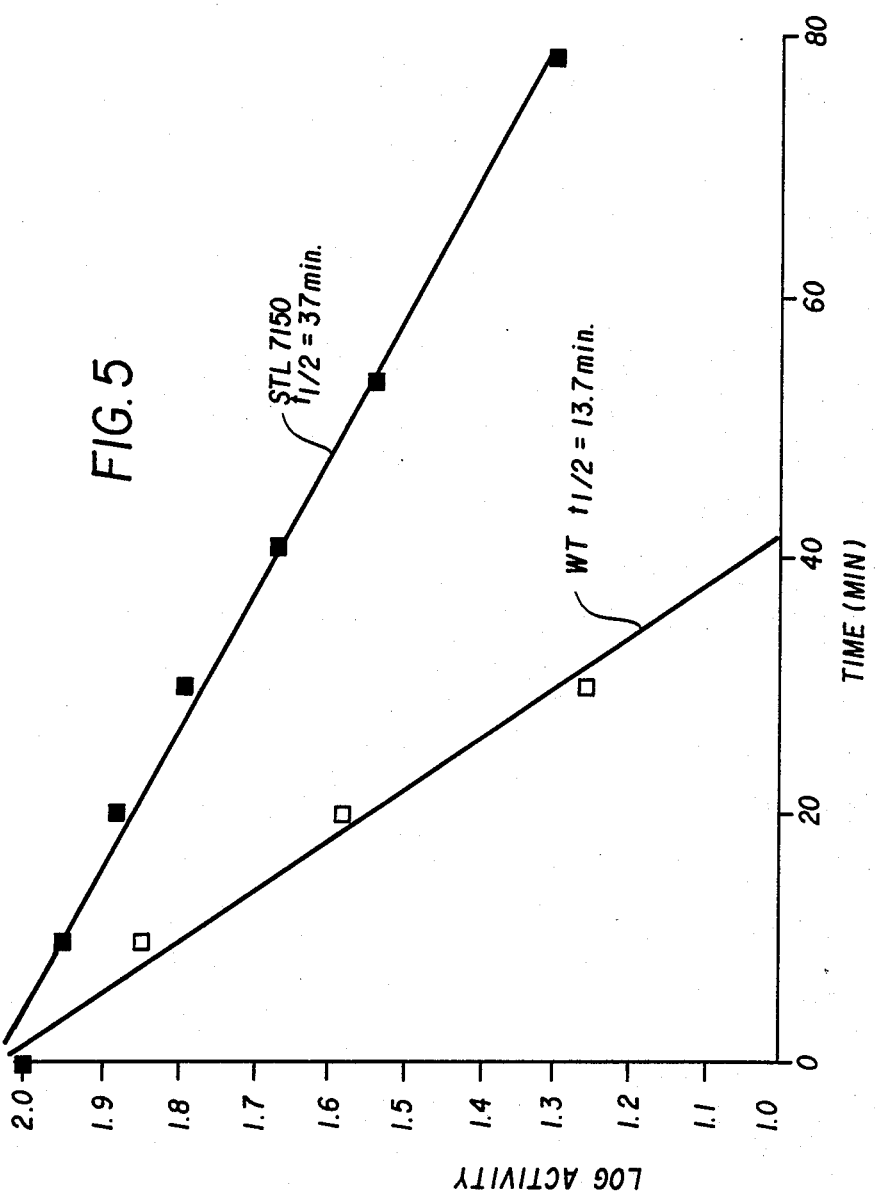
FIG. 5 is a graphic illustration showing thermal inactivation of variant subtilisin according to the invention (7150) and subtilisin wild-type at 45° C. in 1.0 mM EDTA, 50 mM KCl, 50 mM Tris-HCl, pH 8.0.

The enhanced stability of subtilisin 7150 was further demonstrated for a variety of other conditions. For example, the thermal inactivation of subtilisin 7150 and wild type in the presence of 50 mM KCl and 1.0 mM EDTA, pH 8.0, is shown in FIG. 5. It was necessary to do these experiments at 45° C. due to the fact that EDTA negates the known effect of calcium ions in stabilizing subtilisin. Under these conditions, subtilisin 7150 was found to have a half-life almost three times that of the wild-type enzyme.

Figure 6:
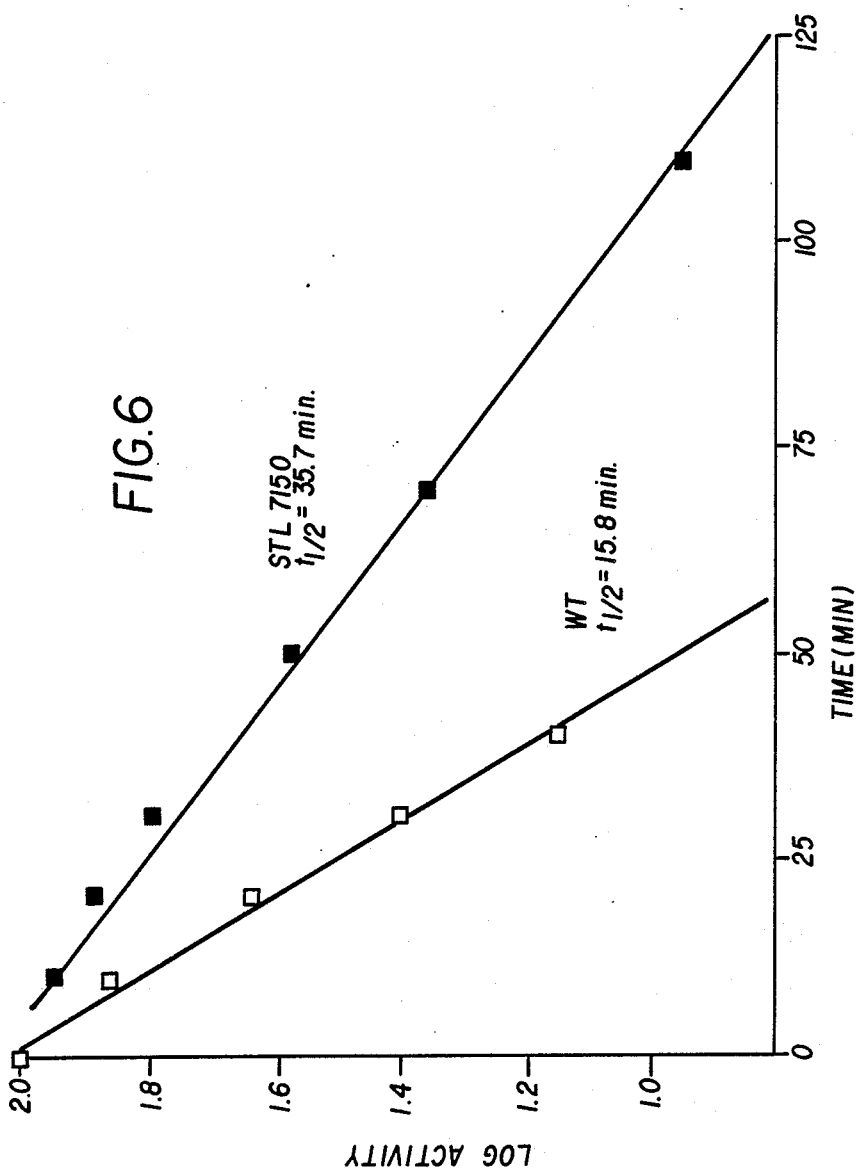
FIG. 6 is a graphic illustration showing thermal inactivation of variant subtilisin according to the invention (7150)and subtilisin wild-type at 40° C., in 1.0 mM EDTA, 20 mM 3-(cyclohexylamino) propanesulphonic acid (CAPS), pH 10.5.

The apparent greater stability of subtilisin 7150 was also found at high pH (10.5) at 40° C. in the presence of 1.0 mM EDTA and protein concentration of 50 ug/ml as shown in FIG. 6.

Differential Scanning Calorimetry

Figure 7:
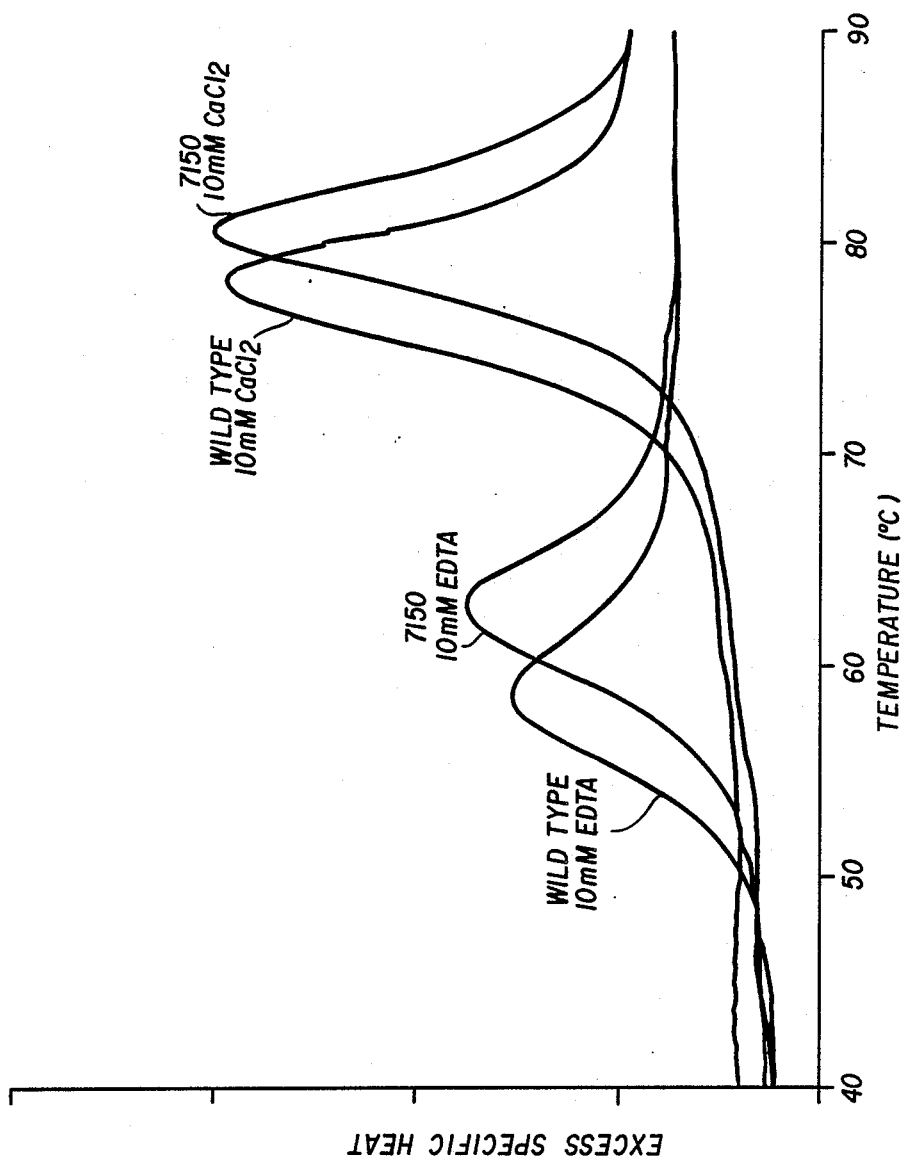
FIG. 7 is a graphic illustration showing differential scanning calorimetry (DSC) profiles for variant subtilisin according to the invention (7150) and subtilisin wild-type at a protein concentration of 3.0 mg/ml (scan rate 60° C./hr.). Samples were scanned in 50 mM Tris-HCl, pH 8.0, 50 mM KCl with either 10mM EDTA or 10 mM $CaCl_2$.

The thermodynamic parameters for the unfolding reaction of subtilisin were obtained through the use of differential scanning calorimetry. The results obtained for subtilisin 7150 and the wild-type enzyme are shown in FIG. 7. The unfolding transition for subtilisin 7150 was found to occur at 80.7±0.1° C. in 50 mM Tris-HCl pH 8.0, 50 mM KCl, and 10 mM $CaCl_2$ some 2.4° higher than that observed for wild-type under identical conditions. In the presence of 10 mM EDTA, the denaturation temperature of subtilisin 7150 was 62.8° C., about 4° C. higher than wild-type subtilisin. These unfolding parameters were obtained by increasing the temperature 60° C./hr. starting at 20° C. and finishing at 90° C. The presence of the competitive inhibitor, N-dansyl-3-aminobenzeneboronic acid at a concentration of 2 mM ($K_i$=2 um at pH 8.0), greatly reduces the amount of autolysis that accompanies the denaturation process for subtilisin.

The increased temperature of denaturation indicates that the substitution of serine for asparagine at position 218 stabilizes subtilisin by increasing the change in free energy for the unfolding reaction.

Stability Studies in Liquid Detergent

For stability studies under alkaline conditions, the subtilisin from B. subtilis strain GX7150 was recovered from a fermentation broth by centrifugation at 7,000 rpm for 30 minutes at 4° C. The subtilisin was then concentrated at 4° C. by the addition of ammonium sulfate (495 g/l ) and the precipitate collected by centrifugation at 12,000 rpm for 30 minutes at 4° C. The pelleted protein was diluted in deionized water to give a concentration of 40,000 Alkaline Delft Units (ADU)/gm. For comparative purposes, a commercial protease, Enzeco (Enzyme Development, New York, N.Y.) was diluted in deionized water to give a concentration of 40,000 $A_{DU/gm}$.

The enzymes were incubated at a concentration of 4,000 ADU/gm in the non-phosphate based, U.S. heavy duty liquid detergent Wisk ® (a registered trademark of Lever Bros. Co., Inc., N.Y., N.Y.) adjusted to pH 10.0. The solutions were incubated at 25° C. for 56 days under these conditions.

Washing tests were performed in a Tergotometer using EMPA-116 (Enzyme Manufacturers Performance Assay from Test Fabrics, Inc., N.Y., N.Y.) as a test fabric. Two grams of Wisk ® detergent with enzyme was added to 1 liter of pH 9.0 deionized wash water. Subsequently, three 6" by 6" pieces of EMPA-116 along with three 6" by 6" pieces of EMPA-221 (unsoiled cloth) were added to the wash water. The wash was performed for 15 minutes at 75 RPM agitation at 55° C. After decanting the wash water, the fabrics were rinsed twice with 1-liter each of cold tap water, dried and lightly ironed. Reflectances of swatches were determined with a Gardner Colorimeter (giving ΔL values). Reflectance was read on both sides of each cloth (a total of 10 readings per cloth). The results are expressed as the mean of 30 ΔL (3 EMPA-116 fabrics) readings for each test. Reflectances were compared to EMPA-116 swatches that were washed, using unmodified subtilisin BPN' and using detergent alone, under identical conditions.

The performance results in the Wisk ® detergent as given in Table I.

TABLE I

| Sample Tested | Day 1 | | Day 35 | | Day 56 | |
| --- | --- | --- | --- | --- | --- | --- |
| | ΔL | % Improve-in Cleaning | ΔL | % Improve-in Cleaning | ΔL | % Improve-in Cleaning |
| Wisk ® | 26.57 | — | 28.51 | — | 26.49 | — |
| Wisk ® + GX7150 Modified Subtilisin BPN' | 39.05 | 47 | 37.60 | 32 | 32.99 | 25 |
| Wisk ® + Subtilisin BPN' | 37.29 | 40 | 34.17 | 20 | 26.44 | 0 |

EXAMPLE V

A mutant designated GX8315 was constructed using three single TM point mutations. The three point mutations were all found by screening randomly mutagenized subtilisin as described above in Example II. The three mutations were Asn218→Ser; Gly131→Asp; and Thr254→Ala. Oligonucleotide mutagenesis (ODM) was used to make these three changes in wild-type subtilisin.

Figure 8:
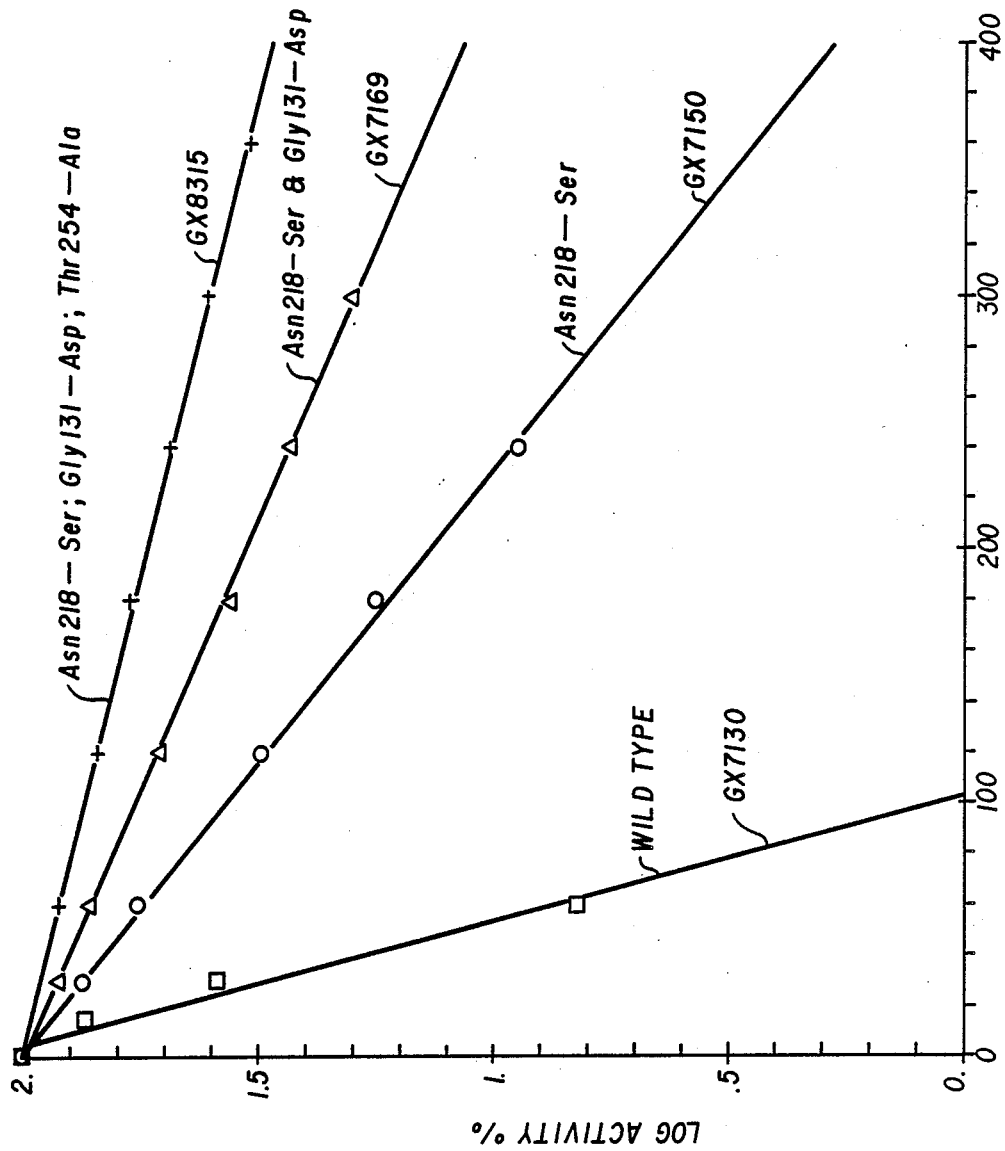
FIG. 8 is a graphic illustration showing thermal stability of variant subtilisins according to the invention and subtilisin wild-type at 70° C. in 10 mM $CaCl_2$, 50 mM Tris- HCl, 50 mM NaCl at pH 8.0.

FIG. 8 shows the effect on thermal stability of some combinations of these mutations. The various proteins were incubated at 70° C. in 10 mM CaCl₂, 50 mM Tris-HCl, 50 mM NaCl at pH 8.0. Aliquots were removed at various times and tested for residual enzymatic activity. Under these conditions, wild-type subtilisin loses half its activity every 19.7 minutes GX7160 is the same as GX7150 but made by ODM.

Mutant GX7160 (Asn218→Ser constructed by mutagenesis) loses half its activity every 71.1 minutes, which is 3.59 times as long as the halftime of wild-type.

Mutant GX7169 (Asn218→Ser and Gly131→Asp) loses half its activity every 127.7 minutes, which is 6.45 times as long as the half-time of wild-type.

Mutant GX8315 (Asn218→Ser, Gly131→Asp, and Thr254→Ala) loses half its activity every 230.3 minutes, which is 11.64 times as long as the half-time of wild-type.

EXAMPLE VI

Differential scanning calorimetry and rate of thermal inactivation, as described in Example IV, were performed on three variants:
7150 ASN 218→SER
7142 GLY 131→ASP
7169 ASN 218→SER
GLY 131→ASP
The results are shown in Table II.

TABLE II

Variants of Subtilisin BPN' That Have Enhanced Stability

| Variant | $\Delta T_m$ (°C.)[a] | | Rate of Thermal Inactivation[b] | |
| --- | --- | --- | --- | --- |
| | 10 mM EDTA | 10 mM CaCl₂ | 1 mM EDTA | 10 mM CaCl₂ |
| 7150 | 3.9 | 2.4 | 2.6 | 3.8 + 0.4 |
| 7142 | — | 0.6 | 1.0 | 1.5 |
| 7169 | 3.4 | 2.9 | 2.2 | 6.2 |

[a] $\Delta T_m$ is the increase in the $T_m$ as measured in a differential scanning calorimetry experiment. The results for two extremes of free calcium concentration, 10 mM EDTA and 10 mM CaCl₂, are shown.
[b] The rates of thermal inactivation are given as multiples of that for the wild type enzyme. The results in 1 mM EDTA were obtained at 45° C., while those in 10 mM CaCl₂ were obtained at 65° C.

These data demonstrate that the effect of single mutations on the free energy of unfolding (as measured by $T_m$) is approximately additive when different single mutations are combined in a single molecule whereas the effect on the rate of inactivation is multiplicative.

EXAMPLE VII

A mutant designated GX7164 was made by oligonucleotide-directed mutagenesis with aspartic acid at location 218. This was done because substitution of serine for asparagine at location 218 had been shown to stabilize subtilisin BPN' Subtilisin 7164 has a half-life for thermal inactivation which is 1.9 times as large as wild-type subtilisin.

What is claimed is:

1. A cloned mutant subtilisin gene coding for a subtilisin polypeptide comprising serine or aspartic acid substituted for asparagine at amino acid position 218 of subtilisin.

2. A cloned mutant subtilisin gene coding for a mutant subtilisin polypeptide comprising serine substituted for asparagine at amino acid position 218 and aspartic acid substituted for glycine at amino acid position 131 of subtilisin.

3. A cloned mutant subtilisin gene coding for a mutant subtilisin polypeptide comprising serine substituted for asparagine at amino acid position 218 and alanine substituted for threonine at amino acid position 254 of subtilisin.

4. A cloned mutant subtilisin gene coding for a mutant subtilisin polypeptide comprising serine substituted for asparagine at amino acid position 218 and serine substituted for glycine at amino acid position 166.

5. A cloned mutant subtilisin gene coding for a mutant subtilisin polypeptide comprising serine substituted for asparagine at amino acid position 218 and aspartic acid substituted for glycine at amino acid position 131 and alanine substituted for threonine at amino acid position 254 of subtilisin.

6. A cloned mutant subtilisin gene coding for a mutant subtilisin polypeptide comprising aspartic acid substituted for glycine at amino acid position 131 of subtilisin.

7. A cloned mutant subtilisin gene coding for a mutant subtilisin polypeptide comprising proline substituted for serine at amino acid position 188 of subtilisin.

8. A cloned mutant subtilisin gene coding for a mutant subtilisin polypeptide comprising glutamic acid substituted for alanine at amino acid position 116.

9. A cloned mutant subtilisin gene coding for a mutant subtilisin polypeptide comprising isoleucine substituted for leucine at amino acid position 126 of subtilisin.

10. A cloned mutant subtilisin gene coding for a mutant subtilisin polypeptide having threonine substituted for serine at amino acid position 53 of subtilisin.

11. A mutant substilisin polypepetide comprising serine or aspartic acid substituted for asparagine at amino acid position 218 of substilisin.

12. A mutant subtilisin polypeptide having serine substituted for asparagine at amino acid position 218 and aspartic acid substituted for glycine at amino acid position 131 of subtilisin.

13. A mutant subtilisin polypeptide having serine substituted for asparagine at amino acid position 218 and alanine substituted for threonine at amino acid position 254 of subtilisin 14. A mutant subtilisin polypeptide having serine substituted for asparagine at amino acid position 218 and serine substituted for glycine at amino acid position 166.

15. A mutant subtilisin polypeptide having serine substituted for asparagine at amino acid position 218 and aspartic acid substituted for glycine at amino acid position 131 and alanine substituted for threonine at amino acid position 254 of subtilisin.

16. A mutant subtilisin polypeptide having aspartic acid substituted for glycine at amino acid position 131 of subtilisin.

17. A mutant subtilisin polypeptide having proline substituted for serine at amino acid position 188 of substilisin.

18. A mutant substilisin polypeptide having glutamic acid substituted for alanine at amino acid position 116.

19. A mutant subtilisin polypeptide having isoleucine substituted for leucine at amino acid position 126 of subtilisin.

20. A mutatnt subtilisin polypeptide having threonine substituted for serine at amino acid position 53 of subtilisin.

21. The mutant subtilisin polypeptide of claim 15 produced by cultivating *B. subtilis* strain GX7150 (ATCC No. 53459).

22. *B. subtilis* strain GX7150 (ATCC No. 53459).

23. A *B. Subtilisin* strain comprising the mutant gene of any one of claims 1 or 2 to 10.

24. A washing preparation comprising the subtilisin polypeptide of any one of claims 11 or 12 to 21.

* * * * *